(12) United States Patent
Guo (10) Patent No.: US 8,021,850 B2
(45) Date of Patent: Sep. 20, 2011

(54) UNIVERSAL TANDEM SOLID-PHASES BASED IMMUNOASSAY

(76) Inventor: Ribo Guo, Acton, MA (US)

( * ) Notice: Subject to any disclaimer, the term of this patent is extended or adjusted under 35 U.S.C. 154(b) by 367 days.

(21) Appl. No.: 12/172,403

(22) Filed: Jul. 14, 2008

(65) Prior Publication Data

US 2010/0009394 A1    Jan. 14, 2010

(51) Int. Cl.
*G01N 33/53* (2006.01)
(52) U.S. Cl. .......................... 435/7.1; 435/7.2; 436/518
(58) Field of Classification Search .................... None
See application file for complete search history.

(56) References Cited

U.S. PATENT DOCUMENTS

| | | | |
|---|---|---|---|
| 4,935,339 A | 6/1990 | Zahradnik | |
| 4,977,247 A | 12/1990 | Fahnestock | |
| 5,009,998 A | 4/1991 | Chow et al. | |
| 5,236,830 A | 8/1993 | Ishikawa | |
| 5,236,849 A | 8/1993 | Ishikawa | |
| 5,296,347 A | 3/1994 | LaMontte | |
| 5,731,158 A | 3/1998 | Bobrow et al. | |
| 5,989,806 A | 11/1999 | Brust | |
| 6,365,418 B1 | 4/2002 | Wagner et al. | |
| 6,498,016 B1 | 12/2002 | Nahar et al. | |
| 2008/0300170 A1* | 12/2008 | Gelber et al. | 514/3 |

OTHER PUBLICATIONS

Janis et al. (Anal. Chem. 1989, vol. 61, p. 1901-1906).*
Duncan MW et al, Proteomics as a tool for clinically relevant biomarker discovery and validation, Experimental Biology and Medicine 230:808-817 (2005).
Kaczmarek E et al, Techniques of image analysis for quantitative immunohistochemistry, Annales Academiae Bialostocensis, 49, 2004, suppl 1:155-158.
Rudolf M. Lequin, Enzyme immunoassay (EIA)/Enzyme-linked immunosorbent assay (ELISA)•, Clinical Chemistry 51(12):2415-2418 (2005).
Massimo Guardigli et al, Chemiluminecence quantitative immunohistochemical determination of MRP2 in liver biopsies, Journal of Histochemistry & Cytochemistry 53(12):1451-1457 (2005).
P Lang et al, Cellular imaging in drug discovery, Nature Review Drug Discovery 5:343-356 (2006).
M. Nisnevitch et al, The solid phase in affinity chromatography: strategies for antibody attachment, J.Biochem Biophys Methods 49(1-3):467-480 (2001).
Pothur R. Srinivas et al, Proteomics for cancer biomarker discovery, Clinical Chemistry 48(8):1160-1169 (2002).
M. W Alid Qoronfleh et al, Use of immunomatrix methods to improve protein-protein interaction detection, Journal of Biomedicine and Biotechnology 5:291-298 (2003).
J. A. Ramos-Vara, Technical aspects of immunohistochemistry, Vet Pathol 42:405-426 (2005).

(Continued)

*Primary Examiner* — Jacob Cheu (57) ABSTRACT

Universal tandem solid-phases based immunoassay (UTSIA) is a sandwich-ELISA equivalent assay for low abundance antigen determination that overcomes limitations of sandwich-ELISA (antibody inactivation by solid phase and strict requirement of a pair of primary and secondary antibodies) by using an affinity binding solid phase to capture antigen specifically from a fluid sample, sequentially dissociating the antigen, transferring, and coating the antigen to a non-affinity binding solid phase for specific antigen determination. Cell-based UTSIA is a cell-based ELISA equivalent assay that overcomes limitations of image method for determining an antigen in the cells or tissue immobilized on a solid phase by dissociating and transferring the detection antibody bound on the antigen of the cells or tissue immobilized on the solid phase to a second solid phase and immobilizing the detection antibody there for specific detection of the antigen via the detection of the detection antibody.

20 Claims, 3 Drawing Sheets

OTHER PUBLICATIONS

Gen Tanaka et al, Fabrication of an antibody microwell array with self-adhering antibody binding protein, Anal Biochem., 350(2):298-303 (2006).

Henri H. Versteeg et al, A new phosphospecific cell-based ELISA for p42/p44 mitogen-activated protein kinase (MAPK), p38 MAPK, protein kinase B and cAMP-response-element-binding protein, Biochem J., 350:717-722 (2000).

A. Voller et al, Enzyme immunoassays with special reference to ELISA techniques, Journal of Clinical Pathology 31:507-520 (1978).

Xiao Yi Yang et al, Development of a quantitative cell-based ELISA, for a humanized anti-IL-2/IL-15 receptor b antibody (HuMikb1), and correlation with functional activity using an antigen-transfected murine cell line, Journal of Immunological Methods, 311(1-2):71-80 (2006).

Ming Zhou et al, Proteomics approaches to biomarker detection, Briefings in Functional Genomics and Proteomics 4(1):69-75 (2005).

Anthony W Arford et al, Expression profiling by high-throughput immunohistochemistry, Journal of Immunological Methods 290:81-92 (2004).

Karen S. Aderson et al, The sentinel within: exploiting the immune system for cancer biomarkers, Journal of Proteome Research 4:1123-1133 (2005).

Rudolf M. Lequin, Enzyme immunoassay (EIA)/Enzyme-linked immunosorbent assay (ELISA), Clinical Chemistry 51(12):2415-2418 (2005).

Peter Matt et al, Biomarker discovery: proteome fractionation and separation in biological samples, Physiol Genomics 33:12-17 (2008).

M. Walid Qoronfleh et al, Use of immunomatrix methods to improve protein-protein interaction detection, Journal of Biomedicine and Biotechnology 5:291-298 (2003).

Steven Bodovitz, Trends in innovation in drug discovery, The Journal of Nuclear Medicine 47(12):19N-20N (2006).

Xiao Yi Yang et al, Development of a quantitative cell-based ELISA, for a humanized anti-IL-2/IL-15 receptor β antibody (HuMikβ1), and correlation with functional activity using an antigen-transfected murine cell line, Journal of Immunological Methods, 311(1-2):71-80 (2006).

Anthony Warford et al, Expression profiling by high-throughput immunohistochemistry, Journal of Immunological Methods 290:81-92 (2004).

* cited by examiner

Fig 1A. Analyte Capture and Detection Mechanism in UTSIA

Fig 1B. Keys for Figure 1A

- ∪ Adaptor molecule
- ∪ Capture molecule
- ● Analyte of interest
- ∩ Detection molecule
- ⚑ Labeled detection molecule

- ★ Label
- ⚑ Labeled molecule against the detection molecule

Detection solid phase

Capture solid phases

Fig 2: Specific Detection and Quantification of Target Antigen (rabbit IgG) by Universal Tandem Solid-phases Based Immunoassay
(Adaptor Molecule: Protein G; Capture Molecule: anti-Rabbit IgG from donkey)

Fig 3A: Antigen Detecting Mechanism of Cell-based UTSIA

Fig 3B: Keys for fig 3A

UNIVERSAL TANDEM SOLID-PHASES BASED IMMUNOASSAY

FIELD OF THE INVENTION

The present invention relates to immunoassay methods for detecting and/or quantitating antigen in a fluid sample, assaying protein-protein interaction in a fluid sample, and detecting and/or quantitating antigen in cells or tissue immobilized on a solid phase.

BACKGROUND OF THE INVENTION

In this post-genomics era, the development of a convenient and robust method for detection and quantitation of low abundance proteins and for analysis of protein-protein interactions is becoming critically important in the fields of biological and biomedical research, clinical diagnostics, environmental and food monitoring, and biotech-pharmaceutical industries (Duncan et al 2005, Srinivas et al 2002, and Albala 2001).

In addition, in the era, the development of a convenient and robust method for cell-based and tissue-based biomarker detection and quantitation is critically important in basic and clinical medicine, biomedical research, and biotech and pharmaceutical industry.

Traditionally sandwich-ELISA is a popular immunoassay to detect and quantitate antigen in biological and non-biological samples (Zangar et al, 2006, Zhou et al 2005). Its applications in clinical diagnostics, bio-medical research, food and environmental monitoring, and biotech and pharmaceutical industries are depended on its advantages: simplicity, sensitivity, and specificity.

Sandwich-ELISA uses specific antigen-antibody affinity binding to detect its antigen (Voller et al 1978, Lequin 2005, and Zangar et al 2006). The basic requirements for the method to detect antigen include having an antigen with at least two binding sites for specific antigen antibody binding reactions, having a pair of matched capture and detection antibodies which can be used to form a sandwich-like complex with the antigen for the antigen's capture and detection, and having a capture antibody with capacity to maintain its antigen binding activity after immobilized on a solid phase. The general procedure for the antigen detection includes that the antigen first reacts with excess solid-phase antibody (the capture antibody) immobilized on a solid phase, after incubation and followed by washing, the bound antigen on the solid phase is reacted with excess labeled antibody (the detection antibody). After further washing, the label is measured, and the signal of the label is directly correlated with the amount of antigen present. A modification of the sandwich-ELISA is the double sandwich-ELISA, which involves a third antibody. The third antibody carries a label and reacts with an unlabeled detection antibody already bound to the antigen. Then the signal of the label is measured, and like before, the signal of the bound label is directly correlated with the amount of the antigen present.

The advantages of sandwich-ELISA are that, by using a capture antibody on a solid phase, the method can enrich and purify an antigen from a fluid sample containing complicated components (this is especially important for the detection of a low abundance protein), and that, by using a pair of capture antibody and detection antibody, the double affinity bindings significantly increase the specificity of the detection. However, in this post-genomics era, to develop a sandwich-ELISA for a protein is still a big challenge for scientists. Why is it so difficult to develop a sandwich-ELISA? Because it is hard to find a capture antibody which maintains the antigen binding capacity after its immobilization on a solid phase, as about 80% of antibodies are denatured after immobilization on the solid phase; and it is even more hard to find a pair of matched capture antibody and detection antibody which form a sandwich complex with an antigen for the successful antigen capture and detection. All of these problems of sandwich-ELISA lead to the assay only can be used in limited number of proteins discovered.

Since Engvall and Perlmann published their first paper on ELISA in 1971 (Lequin 2005), there are many inventions and literatures in the field of immunoassay. However, most of these researches are focused on improvements of sandwich-ELISA, not worked on inventing an alternate convenient and robust immunoassay to overcome the technical difficulty of sandwich-ELISA, the requirement of a pair of perfect matched capture antibody and detection antibody for specific antigen detection and quantitation. For example, U.S. Pat. No. 5,236,849 worked on reducing the label signal background and increasing sensitivity of sandwich-ELISA by adding additional steps of dissociating the antigen-antibody complex from the solid phase and then rebinding the complex to a new affinity solid phase which attached with a reactive group which is capable of specifically binding with the complex; although U.S. Pat. No. 5,236,849 used two solid phases and a dissociating step in its patent claims, the invention does not solve the technical limitations of sandwich-ELISA by following facts: U.S. Pat. No. 5,236,849 uses sandwich complex mechanism of sandwich-ELISA for antigen or antibody's capture and detection; and in dissociating step of U.S. Pat. No. 5,236,849 the complex of antigen and antibody is dissociated from the solid phase in a form of the immunocomplex, not breaking the complex to elute un-complexed antigens into the liquid phase of the Dissociation buffer; in addition, both solid phases of U.S. Pat. No. 5,236,849 used are affinity binding solid phases (in which there is at least an affinity binding component immobilized), which means the method is not an universal method, as the setting of two different affinity binding solid phases for each antigen analysis is very difficult; finally, the detection step of U.S. Pat. No. 5,236,849 focuses on the detection of complex of antigen and antibody, not on the single antigen or single antibody, that is "assaying for the complex, bound to the second solid carrier." (Copied from claim 1C of U.S. Pat. No. 5,236,849). Another example is the patent of U.S. Pat. No. 5,236,830; the inventor also used two solid phases and a dissociating step for antigen assay. But the goal of the invention is to increase the sensitivity of the antigen detection, and the mechanism of the antigen's capture and detection is sandwich-ELISA, and the two solid phases used are all affinity binding solid phases to increase detection sensitivity. Therefore, both U.S. Pat. No. 5,236,830 and U.S. Pat. No. 5,236,849 are not an invention which solves the technical challenge (the requirement of a pair of matched capture antibody and detection antibody for antibody-antigen-antibody complex formation) of sandwich-ELISA. In contradictory, they are a more complicated and two affinity solid phases based sandwich-ELISA, that need several pairs of matched capture antibodies and detection antibodies. Through careful literature searches, it seems all inventions of immunoassay before current invention have not solved the technical limitations of sandwich-ELISA successfully; specifically, they continue using sandwich-ELISA mechanism, the formation of antibody-antigen-antibody complex, to capture and detect/quantitate antigen. Thus, there is a need to invent a convenient and robust method to replace sandwich-ELISA with a novel alternate mechanism for the antigen capture and detection.

As mentioned earlier, to develop a convenient and robust method for analysis of protein-protein interaction is critically important. It is because the protein-protein interactions are at the center of almost every cellular process from cell motility, DNA replication, transcription, translation, splicing, secretion, cell cycle control, signal transduction, cell proliferation, to cell-cell interactions; and because classical and natural method for analyzing protein-protein interactions, the immunoprecipitation (IP), is not a high through put and not a convenient method, as it needs coupling with other assays such western blot and immuno-blotting to get final result. Therefore, there is a need to invent a convenient and robust immunoassay method to replace IP.

Another important immunoassay is immunohistochemistry (IHC) and immunocytochemistry (ICC). IHC is a technique developed by Coons six decades ago (Coons A H C H et al., 1941). Today IHC has a central role in the field of diagnostic medicine and research of pathology. IHC's variation ICC also has important role in biomedical research, clinical diagnostics, and drug discovery. Both techniques of IHC and ICC are using a detection antibody to detect an antigen immobilized on a solid phase. The major difference is that the antigen detected by IHC is located in tissue immobilized on a solid phase, while the antigen detected by ICC is located in cells fixed on a solid phase.

The major challenge of ICC and IHC is that it is difficult to set up quantitative ICC and IHC. Traditionally ICC and IHC are qualitative methods or semiquantitative methods (Kaczmarek E et al 2004, Lang et al 2006, Dodson 2002, Ramos-Vara 2005, Guardigli et al 2005). The presence and amount of the antigen on the tissue or cells immobilized on a solid phase is judged by assigning scores of a skilled observer such as pathologist via using a proper microscope, or by cellular or tissue image method that involves image capture and image data analysis. It is well known that the scores method is not objective; the results from the scores method for quantitation can be varied significantly with different observers. The image method also is not an ideal quantitative method as it is not a direct measurement of antigen quantity, needs expensive equipment, consists of complicated data manipulation procedures that might be leading to false positive, and is very time consuming. Thus, there is an urgent need to develop better method for quantitative ICC or quantitative IHC.

This invention discloses a novel immunoassay method to replace sandwich-ELISA for protein or other antigens' detection and quantitation, and to replace IP for protein-protein interaction analysis. The basic idea of the invention is that by separating the process of antigen capture and detection of sandwich-ELISA in a solid phase into two solid phases-based processes (one affinity binding solid phase and one non-affinity binding solid phase) to break the strict requirement of a perfect matched two antibodies for formation of sandwich antibody-antigen-antibody complex in sandwich-ELISA. The first solid phase (the affinity binding solid phase) of present invention is for the capture of the antigen by affinity binding, and the second solid phase (non-affinity binding solid phase) of present invention is for immobilizing the antigen for specific detection. As the invention need two solid phases and can be used to set up immunoassay for unlimited number of proteins, the invention is named as universal tandem solid-phases based immunoassay (UTSIA).

The invention also discloses an important variant of UTSIA, cell-based UTSIA, for quantitative IHC and ICC. It is a cell-based ELISA equivalent immunoassay which is used to detect and quantitate antigen of interest in cells or tissue immobilized on a solid phase. The advantage of the cell-based UTSIA comparing with cell-based ELISA is that it eliminates the background of cells or tissue of cell-based ELISA in the detection/quantitation step. The applications of the cell-based UTSIA comprise cell based or tissue based biomarker evaluation, detection, and quantitation, in the fields of biomedical research, clinical diagnosis, and drug discovery.

THE DETAIL DESCRIPTION OF THE INVENTION

The following definitions, description of figures, general descriptions, steps, figures, preferred embodiments, and prototype examples are offered by way of illustration of present invention, and not by way of limitation of present invention.

DEFINITIONS

The following definitions are for general reference. If in case that the meaning of a word or phrase in a paragraph of present invention is not consistent with the definitions listed below, or the meaning of a word or phrase is not defined in the definitions listed below, these meanings should be decided by the contents of the paragraph(s) that use the word or phrase.

Adaptor molecule: as used herein, is a molecule which can be immobilized on a solid phase (the first solid phase) to be part of a capture system, wherein the adaptor molecule immobilized on the solid phase is capable of binding a capture molecule and is capable of preventing the inactivation of the capture molecule's antigen binding ability by the solid phase; the adaptor molecule is selected from molecules comprising Protein G, Protein A, Protein A/G, Protein L, antibodies, proteins, recombinant proteins, recombinant antibodies, small organic molecules, peptide, or nucleic acid aptamers. Adaptor molecule comprises site(s) for attaching or coating to a solid phase and site(s) for binding of a capture molecule.

Affinity binding: as used herein, is a binding reaction same as or similar to the specific binding interaction between an antigen and its antibody, or between a ligand and its receptor; the affinity bindings can be disrupted by an dissociation buffer with extreme low or high pH.

Aptamer: as used herein, is a polymer molecule that has high specificity and affinity for its target molecule; it may replace the antibody for UTSIA or UTSIA based assays.

Assaying: as used herein, refers to qualitative or quantitative analysis of a substance.

Capture molecule: as used herein, is a molecule used to capture an antigen being assayed via a affinity binding between a capture molecule and an antigen in a liquid phase or on a solid phase. The capture molecule comprises antibody, recombinant antibody, protein, recombinant proteins, small or big organic molecules, and peptide or nucleic acid aptamers. If the capture molecule is an antibody, then it is named as capture antibody.

Capture solid phase: the capture solid phase is the solid phase immobilized with adaptor molecule and/or capture molecule.

Cell-based UTSIA: as used herein, is a cell-based immunoassay for detecting and quantitating an antigen of interest on cells or tissues immobilized on a solid phase; cell-based UTSIA comprises step of dissociation that transferring the detection antibody from a solid phase immobilized with cells or tissue to a solid phase without cells or tissue.

Chromogen: as used herein, is a substance that lacks definite color but may be transformed into a pigment.

Coating: as used herein, is a physical adsorption process to immobilize substance on a solid phase; in contrast to the affinity binding, the substance immobilized on a solid phase by the coating or the physical adsorption process is nearly not dissociable from the solid phase by buffer with extreme low or high pH.

Detection molecule: as used herein, is a molecule used to detect an antigen on a solid phase via affinity binding between the detection molecule and the antigen. The detection molecule comprises antibody, recombinant antibody, protein, recombinant proteins, small or big organic molecules, and peptide or nucleic acid aptamers. If the detection molecule is an antibody, then it is named as detection antibody and its target substance is an antigen.

Detection solid phase: as used herein, is a solid phase used for immobilizing antigen dissociated from a capture solid phase. The detection solid phase comprises of hydrophobic phase such as polystyrene plate. The detection solid phase is also named as second solid phase.

Determining: as used herein, refers to qualitative, quantitative, or qualitative and quantitative analysis of a substance; determination has same meaning of the determining; assaying also has same meaning of the determining.

Dissociation buffer: as used herein, is a buffer comprising extreme low or high pH (e.g., less than 2.5), which is capable of disrupting affinity binding, and of eluting antigen(s) bound on a capture solid phase into liquid phase.

ELISA: as used herein, is an enzyme linked immuno-sorbent assay.

Fc-domain: as used herein, is the protein or fragment of protein which can bind with Fc-binding protein by affinity binding.

Fc-binding protein: as used herein, is a protein which is capable of binding Fc-domain protein, such as an antibody with a Fc-domain; Fc-binding protein comprising protein-A, Protein G, and any other proteins or other molecules which can specifically bind with Fc-domain of a protein or an antibody; Fc-binding protein can be used as adaptor molecules in UTSIA if the capture molecule is a molecule with Fc-domain.

First solid phase: as used herein, may be the solid phase for making capture solid phase in UTSIA, in which the solid phase is immobilized with affinity molecule; it also may be the solid phase for immobilizing the cells or tissues in cell-based UTSIA.

Fluid sample: as used herein, fluid sample is a fluid that might contain an antigen or antigen-antigen complex to be analyzed, comprising biological fluids, extracts or lysates of cells or tissues, biological samples such as blood, serum, plasma, cerebrospinal fluid, lymphatic fluid, semen, urine, sputum, synovial fluid, saliva, lacrimal tears, nipple aspirate, and eye fluid; fluid samples may be of animal, plant, bacterial, viral, prion, or other life species. For analysis, if a sample is not a fluid, such as the tissue and the organ, the sample can be changed to fluid sample by adding suitable buffer and elements such as proteinase inhibitors and by processing with suitable procedures such as vortex and ultrasonic disruption.

Immobilize, immobilizing, and immobilization: as used herein, is a process or an action of fixing a substance onto a part of solid phase which comprises surface of the solid phase; the process comprises physical adsorption (coating), affinity binding, chemical covalent attachment, or combination of any of the three processes.

HRP: as used herein, is horseradish peroxidase. It is tagged on an antibody for signal production and detection. It is an enzyme that needs a substrate such as TMB to produce a colorful product for the signal detection.

Immuno-complex: as used herein, is the complex of antigen and antibody formed by specific antigen antibody affinity binding.

IP: as used herein, is a method of using a solid phase immobilized with an Fc-binding protein to precipitate or capture an immuno-complex of antibody and antigen from a fluid sample. The antigen obtained from the IP is usually further processed and detected by SDS-PAGE and Western Blot. IP is the abbreviation of immunoprecipitation.

Label: as used herein, is a molecule with a physical property or biochemical activity that is analyzable by a detector via the label's physical property or the label's catalyzed activity; it is usually tagged on a detection molecule or a third antibody against an unlabeled detection molecule for an antigen detection and quantitation; the label comprises dye, fluorescent tag, radioactive isotope, or enzyme; the signal produced from the label itself or mediated by itself, can be fluorescent, chemiluminescent, light-scatting, nano-crystalline, colorimetric, or radioactive, or any combination thereof; in special case, an unlabeled detection molecule or an antigen bound on a detection solid phase can be detected by an instrument, the unlabeled detection molecule or the antigen itself is acted as a label too.

Liquid phase: as used herein, is the fluid phase of a fluid sample, a buffer, or a solution; and it comprises water.

Neutralizing buffer: as used herein, is a buffer with opposite extreme high or low pH of a dissociation buffer. The neutralizing buffer neutralizes the dissociation buffer's extreme pH and brings back the pH to a level that is suitable for an antigen's adsorption on a detection solid phase and that is suitable for affinity bindings; the neutralizing buffer can't contain blocking components which might interfere with the antigen's coating process on the detection solid phase, or might interfere with the affinity bindings.

Protein-protein complex: as used herein, is a complex of multiple proteins; the proteins in the complex bind together via affinity binding interactions; protein 1 and protein 2 are used to define two different proteins which form a protein-protein complex; but protein-protein complex can be consisted of more than 2 proteins, then they can be named as protein 3, protein 4, . . . these proteins such as protein 3 and protein 4 can be detected with UTSIA by using detection molecules against the protein 3 and protein 4.

Protein or polypeptides or peptides: as used herein, are molecules which comprise multiple amino acid residues linked via peptide bonds.

Quantification: as used here, is same as quantitation.

Quantitate: as used herein, is to determine the amount(s) or the concentration(s) of antigen(s) of interest in a fluid sample; has same meaning of quantify; its noun is quantitation; its adjective is quantitative.

(s): as used herein, refers single or multiple; for example, molecule(s) refer to a molecule or many molecules, antigen (s) refer to an antigen or many antigens.

Second solid phase: as used herein, is the detection solid phase in UTSIA for coating the antigen(s) of interest; but for cell-based UTSIA, the second solid phase is the solid phase for immobilizing detection antibody dissociated in the liquid phase of the dissociation buffer.

Sheet: as used herein, is 2-dimensional solid phase comprising membrane, leaf, phase, pane, or slide; wherein the 2-dimensional solid phase is suitable for immobilizing cells or tissue for IHC or ICC.

Solid phase: as used herein, the solid phase comprises plastic, glass, metal, or papers containing a number of regions wherein adaptor molecule, capture molecule, antigen, detection molecule, or sample can be immobilized on its phase, and the solid phase can be used to carry out the steps of UTSIA or cell-based UTSIA.

Stripping buffer: as used herein, is a buffer with extreme pH, such as 0.2 M Glycine pH 2.5; the stripping buffer is used to strip antibodies or detection molecules and molecules against the detection molecules off the detection solid phase.

Signal generating system: as used herein, is a system for detecting a substance of interest bound on second solid phase (it is also named as detection solid phase); the system comprises a labeled detection molecule against the substance, or an unlabeled detection molecule against the substance and a labeled molecule against the unlabeled detection molecule.

TMB solution: as used herein, is the chromogenic reagent for peroxidase, designed for ELISA and UTSIA. It contains 3,3',5,5'-tetramethylbenzidine (TMB), hydrogen peroxide ($H_2O_2$), and other stabilizing agents.

Un-complexed: as used herein, is equal to the meaning of not binding with each other by affinity binding(s).

SUMMARY OF THE INVENTION

The invention of universal tandem solid-phases based immunoassay (UTSIA) relates to a method for determining the presence and the amount of an antigen in a fluid sample and for assaying the presence of an antigen-antigen complex in a fluid sample, which comprises steps of
  (a) using a capture solid phase to capture an antigen or antigen-antigen complex of interest from a fluid sample via affinity binding reaction;
  (b) using a dissociation buffer to release the antigen or antigens bound on the solid phase into a liquid phase in the form of un-complexed antigen(s);
  (c) coating the antigen or the antigens in the liquid phase onto another solid phase by a physical adsorption process; and
  (d) detecting the antigen or one of the antigens coated on the solid phase by using detection molecule(s) specifically recognizing the antigen or one of the antigens.

The invention UTSIA overcomes technical limitations of sandwich-ELISA such as the inactivation of primary antibody by the solid phase and the strict requirement of a pair of primary and secondary antibodies for forming sandwich-like immuno-complex. Therefore, the first application of UTSIA is for low abundance protein determination, especially when the sandwich-ELISA for the determination is not available or not satisfactory. The second application is for protein-protein interaction complex analysis, as UTSIA is capable to capture a protein-protein complex from a fluid sample, dissociating the complex to un-complexed proteins and coating the proteins on a solid phase for specific detections.

One variation of UTSIA is cell-based UTSIA, it detects and quantitates antigen on cells or tissue immobilized on a first solid phase by transferring an antibody bound on the antigen in cells or tissue immobilized on the first solid phase to a second solid phase, and immobilizing the antibody on the second solid phase for detection; as the presence and the amount of the antigen in the cells or tissue immobilized on the first solid phase is directly correlated with the presence and the amount of the detection antibody immobilized on the second solid phase. Therefore, it provides a novel method of quantitative immunohistochemistry and quantitative immunocytochemistry to replace current complicated and un-robust image method of IHC and ICC for antigen quantitation. It is especially useful for cell-based drug discovery in biotech-pharmaceutical industries. It is also useful for cell-based or tissue-based biomarker detection, evaluation, and quantitation in basic and clinical medicine, biomedical research, and other fields.

DESCRIPTION OF THE FIGURES

FIG. 1A. Antigen Capture and Detection Mechanism in UTSIA: 1a, incubating a fluid sample with a capture solid phase (the solid phase immobilized with a capture molecule) to immobilize an antigen on the capture solid phase; 1b, pre-incubating a fluid sample with a capture molecule to form a complex of the antigen and the capture molecule, then contacting the complex with a capture solid phase (the solid phase immobilized with an adaptor molecule) to immobilize the antigen; 1c, incubating a fluid sample with a capture solid phase pre-immobilized with the complex of an adaptor molecule and a capture molecule to immobilize the antigen on the capture solid phase; 2a, adding a dissociation buffer to the capture solid phase to release the antigen to liquid phase and then transferring the liquid phase containing the antigen to a detection solid phase; 2b, adding a dissociation buffer to the capture solid phase to release the antigen to liquid phase and then transferring the liquid phase containing the antigen to a detection solid phase; 3, immobilizing the antigen to the detection solid phase by physical adsorption; 4a, adding a labeled detection molecule to recognize the antigen coated on the detection solid phase for detection and quantitation of the antigen; 4b, adding an unlabeled detection molecule to recognize the antigen coated on the detection solid phase; 5, adding a labeled molecule against the unlabeled detection molecule for the detection and quantitation of the antigen.

FIG. 3A. Antigen Detecting Mechanism of Cell-based UTSIA: 1. a first solid phase immobilized with cells or tissue is incubated with a detection antibody against an antigen of interest to bind the detection antibody on the first solid phase; 2. then the unbound detection antibody is removed, and the first solid phase is incubated with a dissociation buffer (with extreme pH) to release the detection antibody bound on the solid phase into a liquid phase of the dissociation buffer; then the liquid phase containing the detection antibody dissociated from the first solid phase is transferred to a second solid phase to coat the detection antibody on the second solid phase; 3. finally determination of the presence and the amount of the antigen of interest on the first solid phase is decided by detecting the detection antibody coated on the second solid phase via using a labeled antibody against the detection body; the labeled antibody is incubated with the second solid phase which may pre-contain a neutralizing buffer (with opposite pH of the dissociation buffer, the mixture of the dissociation buffer and the neutralizing buffer will get a pH around 7) for proper time, then the unbound is removed, and then the bound labeled antibody is used for signal detection; the signal from the labeled antibody on the second solid phase is correlated with the presence and the amount of the antigen of interest in the cells or tissue immobilized on the first solid phase. Please note: if the detection antibody is labeled with a detectable tag, it can be detected directly on the second solid phase without the step 3 of FIG. 3A.

DETAIL DESCRIPTION OF THE INVENTION

(I) General Description

Immunoprecipitation (IP) is a simple method used to isolate antigen in protein chemistry (Qoronfleh et al 2003). Its principle is that, an antibody (capture antibody) against an antigen is allowed to form an immuno-complex with the antigen in a fluid sample, such as cell lysate. The immuno-complex is then captured on a solid phase to which either Protein A or Protein G has been immobilized. This process of capturing the immuno-complex to the solid phase from a solution is referred as precipitation. Any proteins or substances that do not precipitated by Protein G or Protein A on the solid phase are washed away. Finally the antigen of the bound immuno-complex are eluted from the solid phase and analyzed by SDS-PAGE as well as western blot technology.

Obviously IP and sandwich-ELISA have similarity, that is, both methods use a solid phase to capture an antigen from a fluid sample. But, people familiar with the art of sandwich-ELISA and IP know that IP has better antigen capture system, because the solid phase of IP does not directly coated with the capture antibody (the capture molecule), but instead, using an adaptor molecule Protein G or Protein A immobilized on the solid phase to bind the capture antibody (the capture molecule). As Protein G or Protein A only binds to the Fc-domain of the antibody, it does not interfere with the antigen binding domain, the Fab domain, of the antibody. Due to this special design, the solid phase of IP acts as not only an affinity binding solid phase but also a solid phase preventing the inactivation of the capture antibody's antigen binding capacity. That's why IP can be used for nearly all proteins' isolation if the proteins have specific antibodies which can be used to pull down the proteins by a solid phase immobilized with Protein G or Protein A or other similar adaptor molecules.

Therefore, it's good idea to use IP's antigen capture system to replace sandwich-ELISA's antigen capture system. But in reality it is a difficult challenge, as Protein G or Protein A immobilized on a solid phase binds not only the capture antibody but also the detection antibody. Thus, IP's antigen capturing system does not work in the method of sandwich-ELISA, as it produces false positive results. That is why sandwich-ELISA doesn't use IP's antigen capture system. Please note, in sandwich-ELISA, the capture antibody is physically adsorbed onto the solid phase (this is the coating process or non-affinity binding process). It is convenient to use physical adsorption (coating) to immobilize a capture molecule (e.g., antibody) or an antigen on the solid phase. The greatest advantage of the physical adsorption of antibody or antigen to a solid phase is that the coated molecules such as antibody and antigen on the solid phase are nearly not dissociable (U.S. Pat. No. 5,009,998). However, as the physical adsorption is a random immobilization process, most of the antibodies usually loss most of their antigen binding capacities (78-82%) after coated on the solid phase (Subramanian, A. and Velander, W. H. 1996). In another experiment, Lu (1996) reported that the immobilization of antibody using Protein A resulted in increasing sensitivity 10 times higher than that of random immobilization. Why antibodies inactivated after adsorption on the solid phase? My opinion is that most of the antibodies used today are not screened and selected from the antibodies that already adsorbed on the solid phase. In contradictory, the antibodies are usually screened from the plate coated with antigens. The three dimensional structures of these antibodies will changed to structures that are not optimal for antigen binding after coating on a solid phase and may lead to loss of antigen binding activity. Therefore, it is relatively easy to find antibodies that bind to an antigen coated on a solid phase, but it is relatively difficult to find antibodies that maintain the antigen binding activity after directly coated on a solid phase. In consequence, immobilizing an adaptor molecule such as Protein A or Protein G on a solid phase first, then using the adaptor molecule bound to bind a capture antibody in a liquid phase overcomes the technical challenge of solid phase inactivation of the capture antibody, and this leads to find more antibodies available for capture of antigens from their fluid samples.

Another technology to review is indirect ELISA, an immunoassay specific for an antibody detection (Voller et al 1978 and Lequin 2005). In this method, an antigen is directly immobilized onto a solid phase via physical adsorption. The target antibody in a fluid sample reacts with the antigen bound on the solid phase to form an immuno-complex, and thus the target antibody is captured on the solid phase from a fluid sample. Then a labeled detection antibody with specificity for the target antibody is added and incubated. Following washing off unbound labeled detection antibody, the amount of the target antibody is measured by detecting the signal produced by the label of the bound detection antibody on the solid phase. Similar to sandwich-ELISA, indirect ELISA also has a useful modification, the double indirect ELISA, which involves a third antibody. The third antibody carries a label and reacts with the unlabeled detection antibody already bound to the target antibody. After washing to remove unbound substances, the signal of the label is measured, and the signal of the label is directly correlated with the amount of the target antibody present in the fluid sample.

Unlike sandwich-ELISA, the indirect ELISA is not used to detect the presence of an antigen (Voller et al 1978). This is because that the antigen or protein in a sample such as cell lysate usually exists in a mixture of million of other proteins and other biomolecules such as DNA, RNA, lipids, and carbohydrates; in addition, the antigen usually exists in a very low concentration. Therefore, it is impossible to directly bind enough amount of the target antigen in the sample onto the solid phase of indirect ELISA specifically for further detection. However, I contemplated that it is possible to detect the antigen of low abundance using indirect ELISA if the method is combining with the antigen capture steps of IP or IP-like method mentioned above. Actually and fortunately, the idea is really working Specifically, the antigen separated from the IP or the IP like antigen capture system is dissociated and then coated onto the solid phase of indirect ELISA for further antigen detection. As the antigen separated from the IP antigen capture system is enriched and is relative pure, and in a water based buffer system without blocking agents such as Tween-20 and BSA, it can be adsorbed to a hydrophobic solid phase of indirect ELISA for further detection. This novel combination of IP-like antigen capture system with indirect ELISA antigen detection system forms the core elements of present invention UTSIA.

Obviously, to make the invention works well, it needs to design an efficient antigen capture solid phase system to obtain an antigen from a fluid sample, an simple antigen dissociating system to release the antigen from the capture solid phase, and a detection solid phase to immobilize the released antigen, and a signal generating system to detect the presence and the amount of the antigen bound on the detection solid phase.

To capture an antigen from a fluid sample, the best way is to immobilize the antigen on a solid phase via affinity binding between the antigen and affinity binding molecule(s) (adaptor molecule, capture molecule, or complex of adaptor and capture molecules) attached on the solid phase. Therefore, the choices of solid phase and the affinity binding molecules are critical for setting up the antigen capture solid phase system (capture system).

Now let me talk about the solid phase for the capture solid phase of present invention. The solid phase is insoluble in water based buffer or solution or samples, and stable in extreme low or high pH conditions. Also the solid phase has capacity to attract and immobilize the capture affinity binding molecule directly, has chemical functional groups which can be used to couple the affinity molecules on the solid phase, or has combinations of these properties. Alternately, the solid phase can attain additional coating materials which can be used to physically adsorb or chemically couple the affinity binding molecules to immobilize them on the solid phase. The solid phase comprises plastic, derivative plastic, magnetic or non-magnetic materials, glass, or silicon materials. The solid phase can be in any suitable shape such as plate, membrane, sheet, dipstick, bead, well, chip, and any proper configurations that known to those of ordinary skill in the art.

A preferred embodiment of the solid phase for the capture solid phase comprises polystyrene 96 well plate. The polystyrene plate has hydrophobic surface which is ideal for protein adsorption or coating. Usually the hydrophobic adsorption is the most convenient method to immobilize an affinity binding molecule on a solid phase comparing with other methods such as the covalent chemical coupling.

One embodiment of the affinity binding molecule on the capture solid phase comprises a capture molecule or capture antibody. The capture molecule is coated on a hydrophobic polystyrene solid surface by physical adsorption or coating process. Before and during the coating process, the buffer containing the capture molecule should avoid blocking components such as Tween-20, BSA, and serum, because these blocking components will reduce or prevent the adsorption of the capture molecule on the solid phase. After the solid phase immobilized with the capture molecule, it should be blocked by a buffer containing blocking components such as Tween-20 and BSA to reduce nonspecific binding in late experimental procedures. The advantage of coating the capture molecule on the solid phase is that it is the simplest antigen capture solid phase. The disadvantage of the coating is that it usually inactivates the capture molecule or capture antibody.

In another embodiment of the affinity binding molecule on the capture solid phase comprises an adaptor molecule. The adaptor molecule is immobilized on a solid phase by physical adsorption (coating process), or covalently coupling reaction. The function of the adaptor molecule is acting as an intermediate molecule between the solid phase and the capture molecule to prevent the inactivation of the capture molecule by the solid phase. Therefore, at least one part of the adaptor molecule is capable of immobilizing onto the solid phase by physical adsorption or by chemical coupling reactions, and at least part of the adaptor molecule can bind with the capture molecule by affinity binding reaction. The solid phase comprises hydrophobic solid phase such as polystyrene plate. Before and during the coating process to immobilize the adaptor molecule on a solid phase, the buffer containing the adaptor molecule should avoid blocking components such as Tween-20, BSA, and serum, because these blocking components reduce or prevent the adsorption of the adaptor molecule onto the solid phase. However, after the solid phase immobilized with the adaptor molecule, it should be blocked by a buffer containing blocking components such as Tween-20 and BSA to reduce nonspecific binding in late experimental procedures. The advantage of coating the adaptor molecule on the solid phase is that it prevents the inactivation of the capture molecule on the solid phase by providing proper orientation of the capture molecule or capture antibody on the solid phase. The alternate method of physical adsorption to immobilize an adaptor molecule to a solid phase is covalent coupling reaction. The method is generally more complicated, and therefore, is not preferred for current invention if the physical adsorption working well. There are many publications that describe the chemical coupling reactions to couple affinity binding molecules to a solid phase, the papers to begin with are by Nisnevitch et al 2001 and by Qoronnfleh et al 2003. Alternately, there are commercial solid phase immobilized with adaptor molecule such as Protein G or Protein A/G available, which may cost more from your budget; examples of these commercial solid phases are Reacti-Bind™ Protein G coated 96 well strip plate and Reacti-Bind™ Protein A/G coated 96 well strip plate from Pierce Biotechnology, Inc, Rockford, Ill., USA.

Even though the adaptor molecule is critical for present invention, there are only two ways available to find the adaptor molecule. One is to screen naturally available proteins such as Protein A, Protein G, Protein A/G, and protein L on a solid phase and test whether they can protect the capture antibody from inactivation; another is to make the adaptor molecule by recombinant molecular cloning technology or other technologies. Tanaka G et al (2006) reported that a recombinant Fc-binding protein (E72G3) with self-adhering ability on hydrophobic solid phase is produced by linking the Fc-binding domain of Protein G (G3) and hydrophobic domain of elastin (E72) by a recombinant molecular cloning technology; the E72G3 retains the antibody binding activity after coating on a hydrophobic solid phase. Therefore, the E72G3 and E72G3 like recombinant proteins can be tested to be used as the adaptor molecule for current invention.

After immobilizing the adaptor molecule on the solid phase and blocking the solid phase with proper blocking buffer, there are three ways to capture an antigen from a fluid sample. One way is that a capture molecule reacts with the antigen in the fluid sample first to form a complex of the capture molecule and the antigen in liquid phase; then the liquid phase containing the complex is incubated with the solid phase immobilized with the adaptor molecule to bind the complex via affinity binding interaction between the adaptor molecule and the capture molecule of the complex. This way is especially useful when the fluid sample doesn't contain substances that may interfere with the affinity binding between the adaptor molecule and the capture molecule. For example, if the adaptor molecule is Protein G and the capture molecule is a capture antibody, then a fluid sample such as cell lysate is mixed with the capture antibody first to form an immuno-complex of the antigen and the capture antibody. Because the cell lysate doesn't contain the antibody-like molecules that may directly binds with Protein G, the immuno-complex will efficiently bind to Protein G immobilized on the solid phase. As the interaction between the immuno-complex and Protein G is an affinity binding, it's ideal to including blocking components Tween-20 and/or BSA in the affinity binding process to reduce non-specific and non-affinity bindings. However, the blocking components such as serum can't be used in this step, because it contains immunoglobulin which will block the affinity binding between the capture antibody and Protein G. Another way is that a capture molecule is incubated with the solid phase immobilized with the adaptor molecule first to bind the capture molecule on the solid phase. Because the interaction between the adaptor molecule and the capture molecule is an affinity binding, it is ideal to including the blocking components such as Tween-20 and BSA on the binding reaction to reduce non-specific bindings. If the adaptor molecule is Protein G and the capture molecule is a capture antibody, then the solid phase immobilized with the complex of Protein G and the capture antibody is ready to capture the antigen in a fluid sample without the immunoglobulin-like molecules (the molecule containing Fc-domain) which will bind with Protein G. But if the fluid sample contains the immunoglobulin-like molecules with Fc-domains, then the solid phase immobilized with the complex of Protein G and the capture antibody is not ready to capture the antigen yet. The solid phase must be further blocked with a blocking buffer which contains serum/immunoglobulins to completely block the un-occupied Fc-binding sites of Protein G on the solid phase to prevent un-wanted binding reactions, wherein the serum/immunoglobulin for blocking and the fluid samples are preferred coming from different animal species to prevent cross immuno-binding reactions in late detection steps. It is important to select blocking serum/immunoglobulins from an animal species that will not interfere with the late detection steps. For example, if in late step the detection molecule is an antibody from rabbit, then the blocking serum/immunoglobulins should not get from rabbit. At the moment, the solid phase immobilized with the complex of Protein G and the capture antibody, after being blocked with serum/immunoglobulin, is ready to capture the antigen in the fluid samples. Please note, the antigen may also include antibody. That is, the solid phase can be also used to capture an antibody of low abundance in a complicated substance mixture fluid sample such as plasma or serum. The third way is that a capture molecule, a fluid sample, and a solid phase immobilized with an adaptor molecule are mixed together to form a complex of antigen-capture molecule-adaptor molecule-solid phase to capture the antigen from the fluid sample. Similar to the first way, the fluid sample should not contain substances that interfere with the affinity binding between the adaptor molecule and the capture molecule. For example, if the adaptor molecule is Protein G and the capture molecule is a capture antibody, then a fluid sample (like cell lysate) is mixed with the capture antibody and the solid phase to form an immuno-complex of the antigen, the capture antibody, and Protein G on the solid phase. Because the cell lysate doesn't contain the antibody-like molecules that may directly binds with Protein G, the complex of antigen-capture molecule-adaptor molecule will be efficiently formed on the solid phase. As the interactions among the components of the complex are affinity bindings, it's ideal to including blocking components Tween-20 and/or BSA to reduce non-specific and no-affinity bindings. However, the blocking component such as serum/immunoglobulins can't be used in this step, because it contains immunoglobulins which will block the affinity binding between the capture antibody and Protein G, thus, it inhibits the capture of the antigen from the fluid sample.

Now the antigen is on the solid phase of the capture solid systems. As mentioned previously, the direct detection of the antigen with a detection antibody on the capture solid phase is the technique of the sandwich-ELISA, which is difficult due to the difficulty in finding a perfectly matched pair of the capture antibody and the detection antibody to form a sandwich complex. Therefore, I am not using the sandwich-ELISA to continue the antigen detection; instead, I dissociate the antigen from the capture solid phase by using a dissociation buffer to release the antigen bound, and then transfer the antigen and adsorb the antigen to another solid phase for further detection. The detail procedure is described further in following paragraphs.

After the antigen is immobilized on the capture solid phase, the solid phase is washed by PBS or other water based buffers to remove unbound substances and to clean unbound blocking components such as BSA and Tween-20. Then the solid phase is incubated with a dissociation buffer to release the antigen into the liquid phase of the dissociation buffer from the solid phase. The dissociation buffer comprises a buffer with extreme pH (e.g., 0.2 M Glycine pH 2.5), which is capable of separating the antigen bound on the solid phase into the liquid phase of the dissociation buffer. The mechanism of the dissociation may be the extreme pH will redistribute the charges of hydrophilic functional groups of amino acid residues in the antigen and in the capture molecule, and this may interrupt the affinity bindings between the capture molecule and the antigen; and therefore, the antigen is released into the liquid phase of the dissociation buffer. Please note, as the antigen dissociated from the solid phase needs to be further coated onto the hydrophobic detection solid phase for further detection, the dissociation buffer can't contain blocking components which might interfere with the antigen's coating process, and these blocking components comprise BSA, serum, tween-20, and the like. There may be other mechanisms besides extreme pH that may be helpful to release the antigen bound into the liquid phase, these include salt concentrations, organic solvents, and detergents. Even though present inventor has not tested whether these mechanisms are compatible with present invention UTSIA, the obvious disadvantages of some of the mechanisms such as organic solvents and detergents are that they are not easy to be neutralized and, in addition, some of them may disrupt hydrophobic bindings (physical adsorption) which is critical for present invention. Therefore, their applications in UTSIA should be further cautiously investigated.

Then the dissociation buffer containing the antigen is transferred to a detection solid phase which contains a neutralizing buffer (e.g., 1M Tris/HCl pH 9.0) with opposite extreme pH of the dissociation buffer. The mixing of the dissociation buffer and the neutralizing buffer neutralizes the dissociation buffer's extreme pH and brings the pH to a level that is suitable for the antigen's adsorption onto the detection solid phase, and the pH is suitable for the late binding steps for the detection of the antigen on the detection solid phase. The neutralizing buffer also can't contain blocking components which might interfere with the antigen's coating process on the detection solid phase, and the blocking components comprise BSA, serum, tween-20, and the like. The detection solid phase comprises a solid phase for immobilizing the antigen dissociated in the dissociation buffer, it comprises hydrophobic solid phase such as 96 well polystyrene plates. The detection solid phase does not require the affinity binding molecule (s) immobilized for the capture of the antigen from the liquid phase, so it is different from the capture solid phase, which requires at least an affinity binding molecule (such as the adaptor molecule or the capture antibody) for the capture of the antigen. The detection solid phase immobilizes the antigen by a simple physical adsorption or coating process preferably. Before and during the adsorption or coating process, the detection solid phase can't be incubated with substances that have blocking capacity, such as Tween-20, BSA, and serum, as these substances block the sites of the solid phase for the antigen's adsorption or coating. As mentioned earlier, the dissociation buffer containing the antigen also does not contain these blocking substances. These special buffer conditions promote the physical adsorption of the antigen onto the detection solid phase. Therefore, after proper time of incubation in these conditions, the antigen dissociated in the liquid phase is immobilized onto the detection solid phase for further detection.

You may ask why the antigen dissociated in liquid phase does not coat back to the capture solid phase, but it is coated onto the detection solid phase? It is because that the capture solid phase was blocked previously and there is no way to coat the antigen back on the capture solid phase by physical adsorption, while the detection solid phase is not blocked and its hydrophobic phase is easily to be coated with antigens (like proteins) which also have hydrophobic residues in their molecules. In addition to above reasons, the capture solid phase immobilizes the antigen by affinity binding, but the detection solid phase immobilizes the antigen by physical adsorption (coating process); and furthermore, under extreme pH of the dissociation buffer, the antigen does not bind with the affinity molecule immobilized on the capture solid phase.

In case there are other molecules co-precipitated (co-capture) with the antigen by the capture solid phase system, then these molecules, if they are complexed with the antigen by affinity binding, they are also released to the liquid phase of the dissociation buffer; and the molecules are also coated to the detection solid phase with the antigen. These molecules can be detected on the detection solid phase by their specific detection molecules. If there are multiple molecules need to be coated on a detection solid phase, then a suitable area of the detection solid phase for proper adsorption need to be experimentally optimized. You can image, if the area is too narrow, it may be only part of the molecules can be coated on the solid phase; the coated part of the molecules may be not optimal for further detection.

After the immobilization of the antigen on the detection solid phase, the next step is to remove the unbound substances and then washing the detection solid phase with PBS or other water-based buffers, and to block the detection solid phase by using blocking buffer comprising blocking components such as Tween-20, BSA, and serum. It is important to select blocking serum from an animal species that will not interfere with the detection steps. For example, if the detection molecule is an un-labeled antibody from rabbit, then the blocking serum/immunoglobulins should not get from the rabbit. After blocking, the antigen on the detection solid phase is detected by a signal generating system. The signal generating system is selected from the group comprising a labeled detection antibody or an unlabeled detection antibody and a labeled antibody against the unlabeled detection antibody. If the signal generating system comprises a labeled detection antibody, the antigen immobilized on the detection solid phase is incubated with a solution containing the labeled detection antibody and the blocking components such as BSA, serum, and Tween-20, to let the labeled detection antibody specifically binds on the antigen coated on the detection solid phase. After removing and washing to remove unbound substances from the detection solid phase, the signal from the label on the detection antibody bound on the detection solid phase is detected by an instrument or other suitable means. The label is selected from the group comprising enzyme, chromogens, luminescent compounds, chemiluminescent compounds, radioactive elements, and direct visual labels such as colored microparticles; the label is capable of producing a signal for detection either by itself or in conjunction with one or more additional substances. For example, if the label is enzyme HRP, then the signal is produced by adding its substrate TMB and other substances required for the enzyme reaction under proper time and temperature to form a blue color product, and then the intensity of the color product (thus, the signal of the label) is measured by a spectrometry via detecting its absorbance at 650-655 nm wavelength. The signal is correlated with the presence of the antigen. To determine the amount or the concentration of the antigen, a standard curve of concentrations or amounts vs absorbances is produced by measuring absorbances produced from serial different concentrations or amounts of the antigen on the assay. Comparing with the standard curve, then the concentration or the amount of the antigen in a fluid sample is decided. If the signal generating system comprises an unlabeled detection antibody and a labeled antibody against the unlabeled detection antibody, the antigen immobilized on the detection solid phase is incubated with a solution containing the unlabeled detection antibody and blocking components such as BSA and Tween-20, to let the unlabeled detection antibody specifically binding on the antigen coated on the detection solid phase. After removing and washing to remove unbound substance from the detection solid phase, the labeled antibody against the unlabeled detection antibody is incubated with the solid phase in the presence of blocking components such as Tween-20, BSA, and serum to let the labeled antibody specifically binding on the unlabeled detection antibody bound on the detection solid phase. After removing and washing to remove unbound substance from the detection solid phase, the labeled antibody immobilized on the solid phase is detected by a detector or other means via the label's physical property or the label's catalyzed activity. The label is selected from the group comprising enzyme, chromogen, luminescent compound, chemiluminescent compound, radioactive element, and direct visual label such as colored micro-particle; the label is capable of producing a signal for detection either by itself or in conjunction with one or more additional substances. To determine the amount or the concentration of the antigen, a standard curve of concentrations or amounts vs absorbances is produced by measuring absorbances produced from serial different concentrations or amounts of the antigen on the assay. Comparing with the standard curve, then the concentration or the amount of the antigen in a fluid sample is decided. The advantage of the signal generating system comprising an unlabeled detection antibody and a labeled antibody against the unlabeled detection antibody is that it provides a universal detecting platform for detection of multiple different antigens in multiplex immunoassay or in microarray immunoassay. For example, multiple different antigens immobilized on different spots of a detection solid phase can be detected by their corresponding different detection antibodies from same animal species, and then the unlabeled detection antibodies are detected by a common labeled antibody specifically against these unlabeled detection antibodies. For example, if these unlabeled detection antibodies are monoclonal mouse IgGs, then a common HRP-labeled anti-mouse IgG can be used to detect these monoclonal IgG antibodies.

Now it is clear that UTSIA is a novel and convenient immunoassay which overcomes the technical limitations of sandwich-ELISA in the capture and detection of an antigen from a fluid sample. The UTSIA is not only a sandwich-ELISA equivalent immunoassay but also an immunoassay with more flexible powers and wider applications. You may wonder whether the UTSIA's antigen quantitation can be used in the situation that the antigen of interest is located in the cells or tissue immobilized on a solid phase, such as IHC and ICC. The answer is yes. In IHC and ICC, there are many other substances immobilized on the solid phase, these substances on the solid phase are interfering with the detection of the antigen of the interest. Therefore, currently routine semi-quantitative method of the antigen in IHC and ICC is by image method that involves the image capture and image analysis (Warford et al 2004 and Kaczmarek E et al 2004). As the image method is not a direct antigen measurement like cell-based ELISA, it is not robust, and the quantitation data usually have big variations and might be false positive. Even though the cell-based ELISA is a very nice cells-based antigen quantitation method, it is very difficult to set up as it needs a very high quality antibody to eliminate background noise signals (Versteeg et al 2000, Yang et al 2006). This bottleneck problem is solved by cell-based UTSIA, a variant technology of UTSIA. Specifically, first using an detection antibody binding on the antigen of interest in the cells or tissue immobilized on a first solid phase, then using a dissociation buffer to release the detection antibody bound into a liquid phase of the dissociation buffer, then coating the detection antibody dissociated in the liquid phase onto a second solid phase; finally, an labeled antibody against the detection antibody is used to detect the detection antibody coated on the second solid phase. The presence and the amount of the antigen of interest on the first solid phase is directly correlated with the detection antibody coated on the second solid phase, and thus directly correlated with the signal from the label of the labeled antibody bound on the second solid phase. Therefore, the antigen of interest on the cells or tissue immobilized on the first solid phase is detected by measuring the presence and the amount of the detection antibody coated on the second solid phase. The detail of the UTSIA based antigen detection and quantitation in cells or tissue immobilized on a solid phase will be further described in late paragraphs.

Followings are major applications of UTSIA in different fields. Please note, in following preferred embodiments of the invention, some detail steps or processes that may be missed in their descriptions, such as blocking, dissociating, neutralizing, transferring, coating, washing, or detecting, it should refer back to above paragraphs of general description and refer forward to prototype example for experimental guidance. As indicated before, they are offered by way of illustration of present invention, and not by way of limitation of present invention.

(II) The Preferred Embodiments of the Invention

Figure 1A:
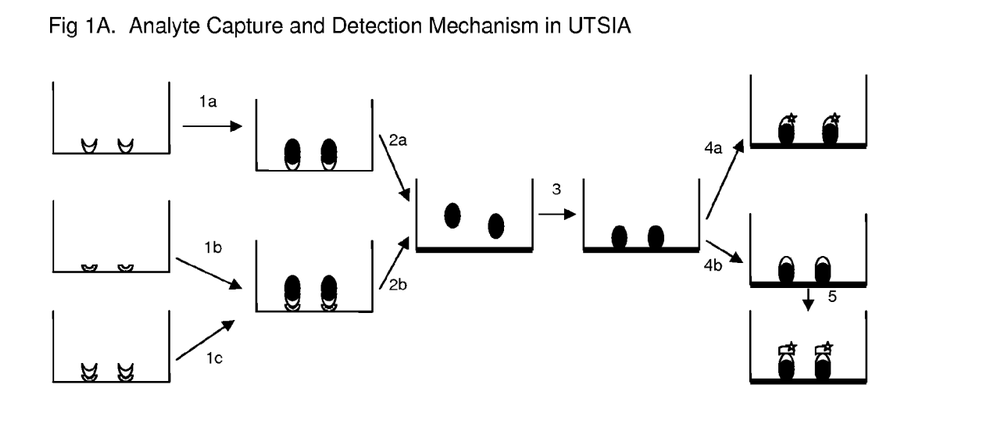
FIG. 1B: Keys for FIG. 1A.
Figure 1B:
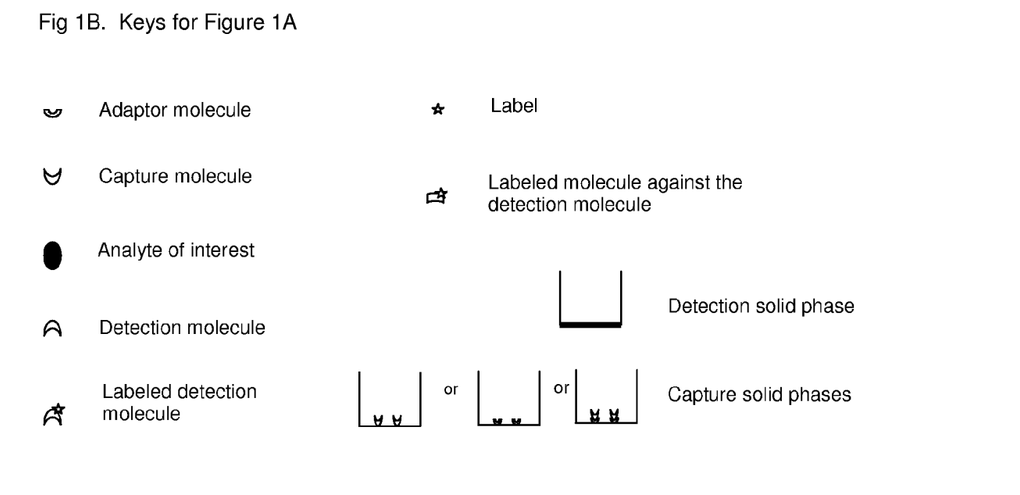
Figure 2:
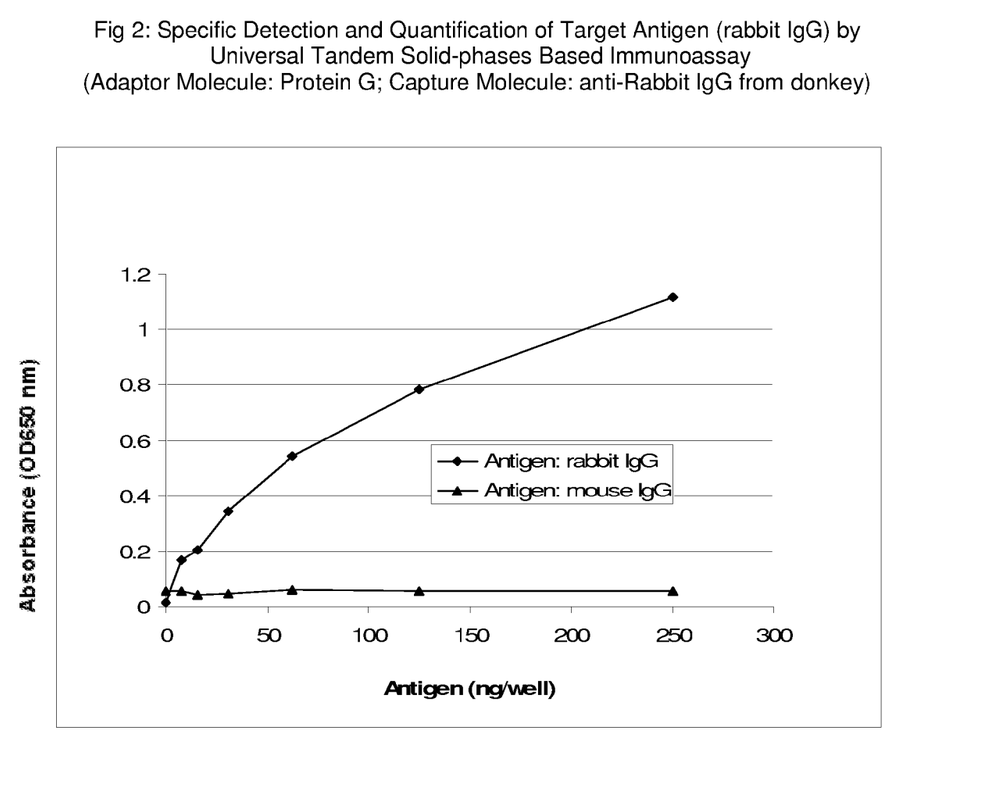
FIG. 2. Specific Detection and Quantitation of Target Antigen (rabbit IgG) by Universal Tandem Solid-phases Based Immunoassay: a prototype example of UTSIA, which demonstrates that the UTSIA specifically detects and quantitates a target antigen (rabbit IgG), but not a control antigen (mouse IgG), in concentration dependent manner.

1. Detecting and Quantitating an Antigen in a Fluid Sample (FIG. 1A, FIG. 1B, and FIG. 2):

Like sandwich-ELISA, UTSIA can be used to detect and quantitate an antigen of interest in a fluid sample. As there are three different capture solid phases, there are several ways to capture and detect an antigen from a fluid sample. A. using a first solid phase immobilized with a capture molecule: the fluid sample is first incubated with the first solid phase to let the antigen immobilized on the first solid phase via the affinity binding between the antigen and the capture molecule immobilized on the first solid phase; after removing and washing to get rid of the unbound substances, the first solid phase is incubated with a dissociation buffer to release the antigen into the liquid phase of the dissociation buffer; then transferring the dissociation buffer containing the antigen to a detection solid phase (second solid phase) which may be pre-incubated with a neutralizing buffer to coat the antigen onto the detection solid phase; after removing and washing to remove the unbound buffer mixture, the detection solid phase is blocked, and then incubated with either a labeled detection molecule to detect the antigen bound via the label of the labeled detection molecule in the presence of blocking components, or an unlabeled detection molecule and a labeled molecule against the unlabeled detection molecule to detect the antigen bound via the label of the labeled molecule in the presence of blocking components; the signal strength of the detection is correlated with the amount or concentration of the antigen in the fluid sample; B. using a first solid phase immobilized with an adaptor molecule: the fluid sample is first incubated with a capture molecule to form a complex of the antigen and the capture molecule in a liquid phase, and then the complex in the liquid phase is incubated with the first solid phase in the presence of blocking components to immobilize the complex via the affinity binding between the capture molecule of the complex and the adaptor molecule immobilized on the first solid phase; after removing and washing to get rid of the unbound substances, the first solid phase is incubated with a dissociation buffer to release the antigen into the liquid phase; then transferring the liquid phase of the dissociation buffer containing the antigen to a detection solid phase (second solid phase) (which may be pre-incubated with a neutralizing buffer) to coat the antigen onto the detection solid phase; after removing and washing to remove the unbound buffer mixture, the detection solid phase is blocked, and then incubated with either a labeled detection molecule to detect the antigen bound via the label of the labeled detection molecule in the presence of blocking components, or an unlabeled detection molecule and a labeled molecule against the unlabeled detection molecule to detect the antigen bound via the label of the labeled molecule in the presence of blocking components; the signal strength of the detection is correlated with the amount or concentration of the antigen in the fluid sample; C. using a first solid phase immobilized with an complex of an adaptor molecule and a capture molecule (the capture molecule is binding with the adaptor molecule pre-immobilized on the first solid phase): the fluid sample is first incubated with the first solid phase to obtain the antigen from the fluid sample in the presence of blocking components, and then after removing and washing to get rid of the unbound substances, the first solid phase is incubated with a dissociation buffer to release the antigen into the liquid phase; then transferring the liquid phase of dissociation buffer containing the antigen to a detection solid phase (second solid phase) (which may be pre-incubated with a neutralizing buffer) to coat the antigen onto the detection solid phase; after removing and washing to remove the unbound buffer mixture, the detection solid phase is blocked, and then incubated with either a labeled detection molecule to detect the antigen bound on the detection solid phase via the label of the labeled detection molecule in the presence of blocking components, or an unlabeled detection molecule and a labeled molecule against the unlabeled detection molecule to detect the antigen bound on the detection solid phase via the label of the labeled molecule in the presence of blocking components; the signal strength of the detection is correlated with the amount or concentration of the antigen in the fluid sample.

2. Determining Protein-Protein Interactions:

As the invention of UTSIA is developed from the technique of IP, another important application of UTSIA is to measure the presence of protein-protein interaction complex in a fluid sample.

Usually the protein-protein complex consists of at least two proteins which bind together via affinity binding(s). The mechanism of UTSIA to determine the presence of the protein-protein complex is via detecting the presence of the proteins of the protein-protein complex on a detection solid phase after pulling down the protein-protein complex by a capture solid phase, dissociating and transferring the proteins from the capture solid phase, and then coating the proteins to the detection solid phase for specific detections.

In previous description, it is clear that there are three different capture solid systems in UTSIA, thus, there are several ways to capture the protein-protein complex from a fluid sample. A. using a solid phase immobilized with a capture molecule: the fluid sample is first incubated with the solid phase to let the protein-protein complex immobilized on the solid phase via the affinity binding interaction between a protein of the protein-protein complex and the capture molecule immobilized on the solid phase in the presence of blocking components; after removing and washing to get rid of the unbound substances, the solid phase is incubated with a dissociation buffer to release the proteins of the protein-protein complex into the liquid phase in a form of un-complexed proteins; then transferring the dissociation buffer containing the un-complexed proteins to a detection solid phase which may be pre-incubated with a neutralizing buffer to coat the protein onto the detection solid phase; after removing and washing to remove the unbound buffer mixture, the detection solid phase is blocked by a blocking buffer, and then incubated with either a labeled detection molecule against one of the un-complexed proteins for signal detection via the label in the presence of blocking components, or a unlabeled detection molecule against one of the un-complexed proteins and a labeled third antibody against the unlabeled detection molecule in the presence of blocking components; the signal strength from the label on the detection solid phase is correlated with the relative amount of the target protein in the protein-protein complex and the amount of the protein-protein complex in the fluid sample; B. using a solid phase immobilized with an adaptor molecule: the fluid sample is first incubated with a capture molecule to form a complex of the capture molecule and the protein-protein complex in the fluid sample, and then the complex is incubated with the solid phase to immobilize the complex via the affinity binding between the capture molecule of the complex and the adaptor molecule immobilized on the solid phase in the presence of blocking components; after removing and washing to get rid of the unbound substances, the solid phase is incubated with a dissociation buffer to release proteins of the protein-protein complex into the liquid phase in a form of the un-complexed proteins; then transferring the dissociation buffer containing the un-complexed proteins to a detection solid phase (which may be pre-incubated with a neutralizing buffer) to coat the un-complexed proteins onto the detection solid phase; after removing and washing to remove the unbound buffer mixture, the detection solid phase is blocked, and then incubated with either a labeled detection molecule against one of the un-complexed proteins for signal detection via the label in the presence of blocking components, or a unlabeled detection molecule against one of the un-complexed proteins and a labeled third antibody against the unlabeled detection molecule in the presence of blocking components; the signal strength of label on the solid phase is correlated with the relative amount of the target protein in the protein-protein complex and the amount of the protein-protein complex in the fluid sample; C. using a solid phase immobilized with an complex of an adaptor molecule and a capture molecule: the fluid sample is first incubated with the solid phase to obtain the protein-protein complex from the fluid sample, and then after removing and washing to get rid of the unbound substances, the solid phase is incubated with a dissociation buffer to release the proteins bound into the liquid phase; transferring the liquid phase containing the proteins to a detection solid phase (which may be pre-incubated with a neutralizing buffer) to coat the proteins onto the detection solid phase; after removing and washing to remove the unbound buffer mixture, the detection solid phase is blocked, and then incubated with either a labeled detection molecule against one of the un-complexed proteins for signal detection via the label in the presence of blocking components, or an unlabeled detection molecule against one of the un-complexed proteins and a labeled third antibody against the unlabeled detection molecule in the presence of blocking components; the signal strength of label on the solid phase is correlated with the relative amount of the target protein in the protein-protein complex and the amount of the protein-protein complex in the fluid sample.

After determining the presence of first protein in the protein-protein complex, it's time to determine the presence of the second protein on the detection solid phase. The first step of the determination is to remove the labeled detection molecule against the one protein of the un-complexed proteins from the detection solid phase, or remove the unlabeled detection molecule against one of the un-complexed proteins and the labeled third antibody against the unlabeled detection molecule from the detection solid phase. This is done by incubating the solid phase with a stripping buffer, usually comprising a buffer with extreme pH, which disrupts the affinity binding of the detection molecule or detection antibody with the protein coated on the solid phase, and therefore, the detection molecule or antibody are removed from the detection solid phase. After washing, the detection solid phase is blocked, and then incubated with either a labeled detection molecule against another protein of the un-complexed proteins for signal detection via the label in the presence of blocking components, or a unlabeled detection molecule against the second protein of the un-complexed proteins and a labeled third antibody against the unlabeled detection molecule in the presence of blocking components; the signal strength for the label on the solid phase is correlated with the relative amount of the target another protein in the protein-protein complex and the amount of the protein-protein complex in the fluid sample.

If there are additional proteins in the protein-protein complex, then above stripping and detection steps can be repeated using either a labeled detection molecule against the additional protein of the un-complexed proteins for signal detection via the label, or a unlabeled detection molecule against the additional protein of the un-complexed proteins and a labeled third antibody against the unlabeled detection molecule; the signal strength for the label is correlated with the relative amount of the target additional protein in the protein-protein complex and the amount of the protein-protein complex in the fluid sample.

3. Detecting Multiple Antigens (UTSIA Based Antibody Microarray):

As mentioned in the background of the invention, the antibody based microarray is a concept that intents to detect multiple proteins in a same assay. However, except in rare case such as cytokines, it is suggested that it is nearly impossible to setting up an antibody-based microarray to detect hundreds of proteins in same time and in same assay with current methods (Zangar et al 2006). It is because every protein has its unique amino sequence and unique 3-dimensional structure, and thus, it is thought that every protein will need a special set of assay conditions such as antibodies, buffer and incubation time for its detection. Indeed, until today the availability of commercial antibody-based microarray is limited, only sandwich-based antibody microarray for the detection of a few proteins such as cytokines available (please note, in this case, the microarray is developed from commercial available sandwich-ELISA for cytokines analysis). Therefore, to make the antibody-based microarray for multiple proteins detection possible, an alternate capture and detection mechanism other than the sandwich-ELISA is required.

UTSIA, different from the sandwich-ELISA, has many universal properties that make the setting up of antibody-based microarray for multiple proteins detection practical. One is that an adaptor molecule such as Protein G on a capture solid phase prevents the capture antibody's inactivation by the solid phase; because the adaptor molecule provides the antibody immobilized on the solid phase in an oriented manner. Another is that UTSIA uses two solid phases, a capture solid phase and a detection solid phase, to replace sandwich-ELISA's requirement of a perfect pair of the capture antibody and the detection antibody for sandwich complex formation; the third is that UTSIA uses a dissociation buffer with extreme pH to disrupt the affinity binding between the capture antibody and the antigen of interest on the capture solid phase, that lead to the antigens can be transferred and further coated on another solid phase, the detection solid phase, for specific detection by a detection antibody. Finally, the detection molecule bound on the detection solid phase is detected by a common labeled third antibody against the detection molecule for signal measurement. Therefore, these universal steps of capture, dissociating, coating, and detection make the UTSIA realistic for multiple antigens detections, such as scaled up to microarray format to detect and quantitate multiple antigens in a same time and in a same assay.

UTSIA based antibody microarray comprises a capture solid phase immobilized with an adaptor molecule such as Protein G, wherein the adaptor molecule is coated on discrete separated regions on the solid phase. To capture multiple antigens from a fluid sample, the discrete separated regions of the solid phase pre-coated with the adaptor molecule are incubated with fluid mixtures of the fluid sample and the different capture antibodies targeting on different antigens in the presence of blocking components, wherein each discrete separated region of the solid phase pre-coated with the adaptor molecule is incubated with a mixture of the fluid sample and a capture antibody. The multiple antigens can be immobilized on the discrete separated regions via the affinity binding interactions between the capture antibodies and the adaptor molecule Protein G immobilized on the solid phase. After washing the solid phase to remove unbound substances, a dissociation buffer is added to these different regions on the solid phase to elute these antigens into liquid phases, with each liquid phase contains an antigen released from a discrete region of the capture solid phase; and then the antigens in the liquid phases are transferred and coated to discrete regions of a detection solid phase (which may pre-contain neutralizing buffer on these regions). After washing and blocking, the coated antigens on the discrete regions of the detection solid phase are then detected by different detection antibodies (each antigen in each region incubated with its corresponding detection antibody) in the presence of blocking components. All detection antibodies are from a same animal species and are from a different animal species of making capture antibodies to avoid cross immuno-reactions. Then, proper amounts of a common labeled third antibody against these different detection antibodies (such as anti-mouse IgG-HRP if the detection antibodies are mouse monoclonal antibodies) are added to these regions of the detection solid phase for the antigens' detections in the presence of blocking components. The strengths of the signals of the label on the discrete regions of the detection solid phase are correlated with the amount of these different antigens in the fluid sample.

Figure 3A:
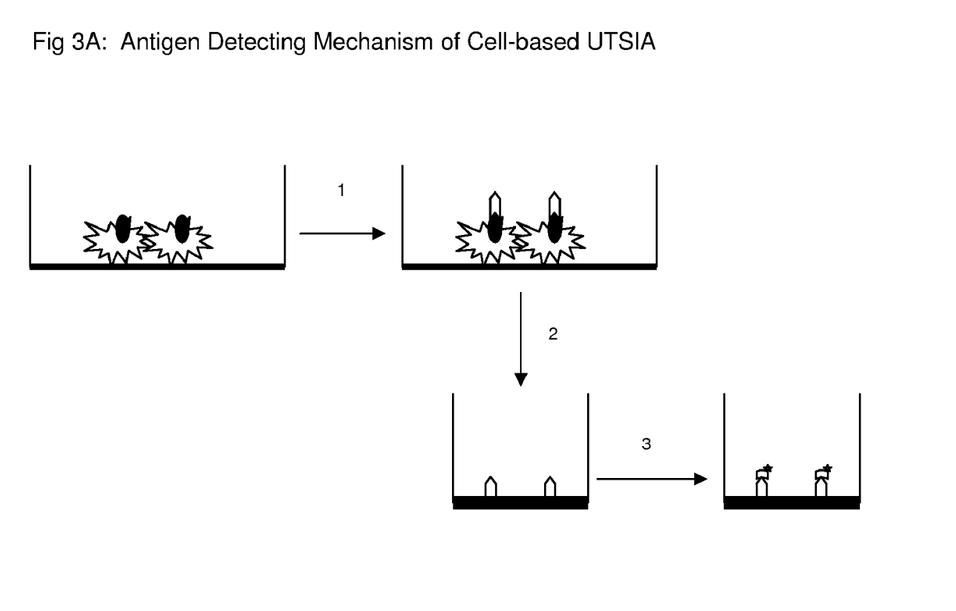
FIG. 3B. Keys for FIG. 3A.
Figure 3B:
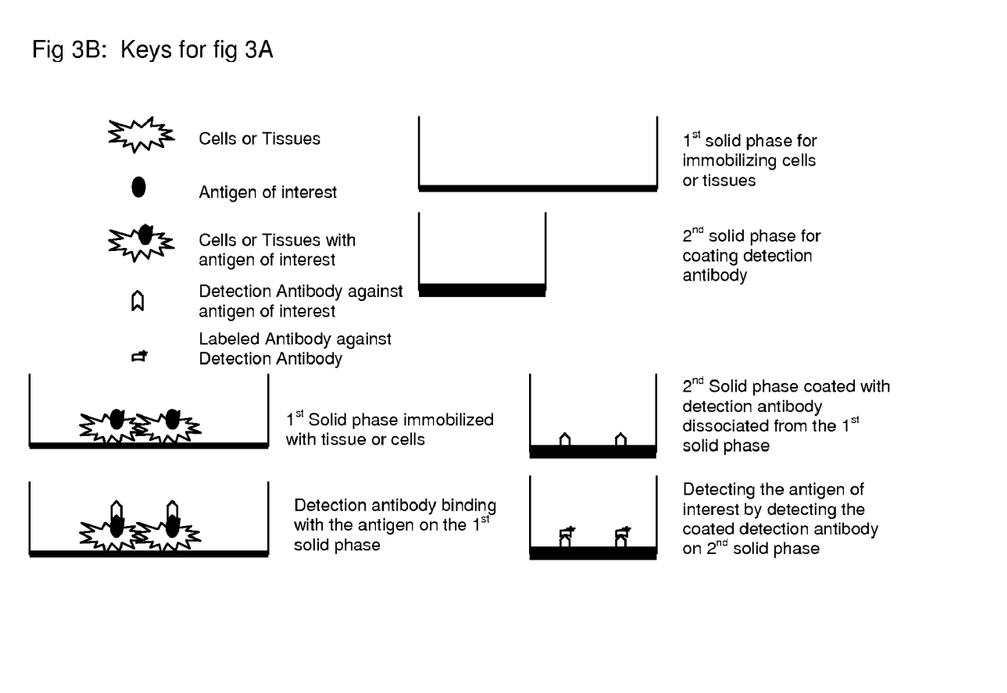

4. Cell-Based UTSIA (FIGS. 3A and 3B):

As mentioned in background, there is an urgent need to develop better method for quantitative ICC or quantitative IHC than the score method and the imaging method. The cell-based UTSIA is a solution to the urgent need. Instead of taking images from the labeled antibody bound on tissue or cells immobilized on the solid phase of IHC or ICC to quantify the antigen of interest, cell-based UTSIA uses a dissociation buffer to release the detection antibody bound on cells or tissue immobilized on the solid phase (first solid phase) to a liquid phase of the dissociation buffer, then transfers the liquid phase to a second solid phase that may contain a neutralizing buffer to coat the detection antibody dissociated in the liquid phase on the second solid phase; this way, the detection antibody originally bound on the cells or tissue of the first solid phase is purified and dissociated from the cells or tissue fixed on the first solid phase, and then is coated on the second solid phase, and this will increase final detection specificity; since the detection of the detection antibody on the second solid phase (instead of the detection of the detection antibody on the first solid phase) avoids non-specific background signals of the cells or the tissue immobilized on the first solid phase. In addition, if the area of the solid phase (the first solid phase immobilized with cells or tissue) is bigger than area of the second solid phase (the solid phase for coating the detection antibody), the detection antibody is also enriched on the second solid phase and this increases final detection sensitivity (since the bigger area of the first solid phase, it will immobilize more cells, so it will have more antigen of interest, thus it will bind with more detection antibody; when the detection antibody is coated to a smaller area of a second solid phase, it is enriched). Then the detection antibody coated on the second solid phase can be detected directly if is pre-labeled, or it can be detected indirectly by incubating with a labeled secondary antibody against the detection antibody. Finally the determining antigen of interest is via detecting the signal of the label immobilized on the second solid phase, and the signal strength of the label is directly correlated with the amount of the antigen of interest on the cells or tissue immobilized on the first solid phase.

Followings are further guidance of cell-based UTSIA for your reference which comprises: growing cells in a 96 well tissue culture plate (first plate or first solid phase) until the cells are near completely confluent; removing the medium from the well; washing with PBS; fixing the cell with 4% paraformaldehyde solution for proper time; removing the paraformaldehyde and washing the fixed cells with PBS; permeabilizing the fixed cells with cold methanol or PBS with 0.5% Triton X-100; blocking the cells with blocking buffer which comprises Tween-20, BSA, and serum; the serum is not from the species from which the detection antibody was taken and the serum is preferred from the species from which the secondary antibody was taken; incubating the cells with an detection antibody against an antigen of interest in a blocking buffer comprises Tween-20 and BSA; removing the antibody and washing the cells with PBS; adding a dissociation buffer with extreme pH to release the detection antibody bound on the antigen of interest on the cells fixed in the well of 96 well plate into the liquid phase of the dissociation buffer; transferring the liquid phase to a well of another 96 well polystyrene plate (second plate or second solid phase) which pre-contains a neutralizing buffer with opposite pH of the dissociation buffer to make buffer mixture with pH optimal for the detection antibody to be detected in late steps of the assay; gentle rotating the plate to coat the detection antibody on the well of the plate; removing the buffer mixture from the well and washing with PBS; blocking the well with a blocking buffer with Tween-20, BSA, and serum; incubating the well with an antibody-HRP against the detection antibody bound in the well of the plate in the blocking buffer comprising Tween-20 and BSA; removing unbound antibody-HRP and washing the well with PBS; adding TMB substrate solution to the well of the second plate and incubating without light for proper time; the signal of the antigen of interest in the cells fixed on the first plate is determined by detecting the absorbance of the second plate by reading the OD650 nm.

There is alternate way to do cell-based UTSIA, which comprises: growing cells in a 96 well tissue culture plate (first plate or first solid phase) until the cells are near confluent; removing the medium from the well; washing with PBS; fixing the cells with 4% paraformaldehyde solution for proper time; removing the paraformaldehyde and washing the fixed well with PBS; permeabilizing the fixed cells with cold methanol or PBS with 0.5% Triton X-100; blocking the cells with blocking buffer which contains Tween-20, BSA, and serum; incubating the cells with a labeled detection antibody against an antigen of interest in the blocking buffer; removing the unbound labeled detection antibody and washing the cells with PBS; then adding a dissociation buffer with extreme pH to release the labeled detection antibody bound on the antigen of interest on the cells fixed in the well of 96 well plate into the liquid phase of the dissociation buffer; transferring the liquid phase to a well of another 96 well polystyrene plate (second plate or second solid phase) which pre-contains a neutralizing buffer with opposite pH of the dissociation buffer to make buffer mixture with pH optimal for the labeled detection antibody to be detected; gentle rotating the plate to coat the labeled detection antibody on the well of the plate; removing the buffer mixture from the well and then washing with PBS; the signal of the antigen of interest in the cells fixed on the first plate is determined by detecting the presence and the amount of the labeled detection antibody coated on the second plate (second solid phase). Please note, the success of the alternate way of cell-based UTSIA depends on whether the label of the labeled detection antibody maintains its activity after the antibody coated on the second plate. However, if the activity of the label is lost during the coating process, the labeled detection antibody coated on the second plate still can be detected by using a labeled antibody against the inactivated labeled detection antibody.

All above steps of cell-based UTSIA can be run on room temperature if the antigen fixed and antibodies used are stable in room temperature; you can optimize the protocols by modifying any steps of the protocols or by adding steps or by reducing steps that lead to better sensitivity and specificity to detect your antigen of interest. In summary, the detail steps and the experimental procedures for detection of each antigen of interest should be tested by experiments and referenced with the general guidance in this chapter. The dissociation buffer is 0.2 M Glycine pH 2.5, and neutralizing buffer is 1M Tris/HCl pH 9.0; PBS is phosphate buffered saline pH 7.0, PBST is PBS with 0.05% Tween-20; blocking buffer is PBST with 1% BSA (bovine serum albumin), or blocking buffer is PBST with 10% goat serum if the detection antibody is not an antibody from a goat; and TMB solution (Sigma T8665) is the substrate for HRP tagged on an antibody. The first solid phase is the polystyrene plate for tissue culture or the polystyrene sheet such as Permanox and Polystyrene Microscope Slides from Electron Microscopy Sciences for tissue immobilization, and the second solid phase is the polystyrene plates for ELISA (Sigma #6562, high protein binding ELISA plate).

After determining the presence and the amount of the antigen of interest on the first plate (first solid phase), it is now critical to get an internal normalization control data from a substance in the tissue or cells immobilized on the first solid phase that the substance is directly correlated with the presence and the amount of the cells immobilized on the first solid phase. The substance comprises proteins, carbohydrates, and DNA/RNA. There are many methods to detect the presence and the amount of these substances, one of the convenient methods is using Bicinchoninic Acid (BCA) protein assay (Stoscheck, C M. 1990) to detect the presence and the amount of the proteins on the cells or tissue immobilized on the first solid phase.

The detail steps of the BCA assay for cells or tissue immobilized on a solid phase are described here: the cells/tissue immobilized on the first solid phase is washed with PBS to clean the dissociation buffer left, then after removing PBS from the cells or the tissue immobilized, 100 ul/well BCA mixtures (A:B=50:1) (PIERCE #23225 BCA Protein Assay kit) is added to the well immobilized with cells/tissue on the first plate; the plate is incubated at 37° C. for proper time to develop purple product solution which the color density is directly correlated with the presence and the amount of the proteins, and thus correlated with the amount of cells/tissue immobilized on the first solid phase. The color product solution of the BCA Protein Assay on the first plate is detected by measuring absorbance at OD562 nm.

Now we get the amount of the antigen of interest and the amount of proteins as the internal normalization control. Dividing the amount of the antigen by the amount of the proteins gets a ratio number that can be used to compare with other data of the antigen got from other samples (if the protein amounts per cell from these samples are comparable), as the data are normalized amounts of the antigen of interest in the cells/tissues immobilized on the first plate.

Besides above internal normalization control, it may also need a negative control for cell-based UTSIA; this can be done by using a non-specific IgG which is from a same animal species of the detection antibody (IgG) to stain the tissue or cells, then follows above described steps to dissociate, transfer, coat the non-specific IgG on a second plate for determination of the non-specific IgG; this non-specific IgG level on the second plate acts as a negative control for the detection antibody.

Cell-based UTSIA is especially useful for cell-based drug discovery, because the method is a simple and robust cell-based assay, and can be scaled up to high through put by adapting to automation. For lead drug candidate screening, the compound is added in the cells growing on the 96 well plate for proper time, and then removing the treatment medium, and running the cell-based UTSIA as above instructed to detect the antigen of interest. The cells without treatment or only treated with the vehicle is also running cell-based UTSIA as a negative control. If there is a significant signal difference between the control and the treatment cells on the antigen of interest, then the compound deserves further validations.

In this post-genomic era, there are many discussions that the future medicine will be a "personalized medicine". The main idea of "personalized medicine" is that the diagnosis, treatment, prognosis, and prevention will all depend on the exact target that causing the disease. That suggests that the detection and quantitation of the target or its related biomarker(s) on cells/tissue will be critical for future medicine. As described above, the cell-based UTSIA has unique property that compliments with current routine IHC and ICC, specifically on the field of quantitation, it will has critical role in current and future medicine.

EXAMPLE OF THE INVENTION

UTSIA Invention Prototype Example

To Detect and Quantitate an Antigen in a Fluid Sample (FIG. 2)

I. Materials and Agents:

The capture solid phase (first solid phase) and the detection solid phase are transparent 96 well polystyrene plates for ELISA (Sigma #6562, high protein binding ELISA plate), the adaptor molecule is Protein G (BioVision #6510-5), dissociation buffer is 0.2 M Glycine pH 2.5, and neutralizing buffer is 1M Tris/HCl pH 9.0, PBS is phosphate buffered saline pH 7.0, PBST is PBS with 0.05% Tween-20, $1^{st}$ blocking buffer is PBST with 1% BSA (bovine serum albumin), and $2^{nd}$ blocking buffer is PBST with 10% goat serum, and TMB solution (Sigma T8665) is the substrate for HRP tagged on the detection antibody. The fluid sample is PBS with 1% BSA containing an antigen rabbit IgG (Santa cruz #sc-577) and a background control antigen mouse IgG (Santa cruz #sc-46680). The capture molecule to the antigen rabbit IgG is anti-rabbit IgG from donkey (Chemicon #AP182). The labeled detection molecule is an anti-rabbit IgG-HRP from donkey (Amersham Biosciences #NA934V). The detection molecule to the control antigen mouse IgG is anti-mouse IgG-HRP from sheep (Amersham Biosciences #NA931V).

II. Procedures:

1. Immobilizing the capture molecule Protein G to the capture solid phase: In the well of 96 well polystyrene plates (first solid phase), 100 µl of (200 ng) Protein G per well in PBS is loaded and incubated for 1 hour at room temperature. Then the unbound fluid is washed away by two time 300 µl/well PBS washing, and then the solid phase is blocked by 1% BSA in PBS 200 ul/well for 15 min.
2. Immobilizing a capture molecule to the capture solid phase coated with Protein G: A capture molecule, anti-rabbit IgG from donkey (Chemicon #AP182), is diluted 10 times (1:10 dilution) with $1^{st}$ blocking buffer, then the diluted capture molecule solution 100 ul/well is incubated in the capture solid phase immobilized with Protein G at room temperature for 30 min, then unbound is removed; then the solid phase is blocked with 10% goat serum PBST for 10 min in room temperature; and then the solid phase is washed by PBST 1 time;
3. Capturing an antigen of interest from a fluid sample onto the capture solid phase: a fluid sample 100 µl/well containing an antigen rabbit IgG or containing a control antigen mouse IgG is added to the capture solid phase, and incubated for 30 min at room temperature. The unbound fluid sample is removed and washed by PBS 300 µl/well for 2 times.
4. Dissociating the antigen from the capture solid phase into the liquid phase: the dissociation buffer 110 µl/well is added to the capture solid phase immobilized with the antigen and incubated in room temperature for 10 min with gentle rotation to separate the bound antigen from the capture solid phase into the liquid phase of the dissociation buffer.
5. Transferring the dissociated antigen and coating it to a detection solid phase: the dissociation buffer with the dissociated antigen is transferred to the detection solid phase having 20 µl of the neutralizing buffer, then the buffer mixture containing the dissociated antigen is mixed and incubated in the detection solid phase for 30 min at room temperature with gentle rotation to immobilize the antigen onto the detection solid phase. After removing the buffer mixture, the detection solid phase is blocked with 200 µl $2^{nd}$ blocking buffer each well for 15 min, then the blocking buffer was removed.
6. Detecting the antigen on the detection solid phase with a detection antibody against the antigen: a labeled detection antibody (anti-rabbit IgG-HRP) against the antigen rabbit IgG 1:5000 at 100 µl/well in $2^{nd}$ blocking buffer, or a labeled detection antibody (anti-mouse IgG-HRP) against the control antigen mouse IgG 1:5000 at 100 µl/well in $2^{nd}$ blocking buffer, is incubated with the detection solid phase immobilized with the antigen for 30 min. The unbound is removed by PBST 300 µl/well washing 3 times. Then the TMB solution 100 µl/well is added to the solid phase and is incubated without light for 30 min. The signal of the antigen on the detection solid phase is detected by reading the OD655 nm.

III. Results

The target antigen (rabbit IgG), but not control protein mouse IgG, is specifically detected and quantitated by UTSIA in a concentration-dependent manner.

I claim:

1. A sandwich-ELISA equivalent immunoassay for detecting and quantifying an analyte in a fluid sample without sandwich-ELISA's strict requirement of a pair matched antibodies, the universal tandem solid-phases based immunoassay (UTSIA), which comprises:
   (a) an affinity binding based specific analyte capture process to immobilize the analyte in the fluid sample on a solid phase via contacting the fluid sample with an affinity binding solid phase;
   (b) a dissociation process to release the analyte immobilized on the affinity binding solid phase into a liquid phase via incubating the analyte immobilized on the affinity binding solid phase with a dissociation buffer;
   (c) a non-affinity physical absorption process to coat the analyte released in the liquid phase on a solid phase via incubating the analyte released in the liquid phase with a non-affinity binding solid phase;
   (d) an affinity binding based specific analyte detection process to detect the analyte via incubating the analyte coated on the non-affinity binding solid phase with a labeled detection molecule to form a complex of the analyte and the labeled detection molecule on the solid phase, or via incubating the analyte coated on the non-affinity binding solid phase with an unlabeled detection molecule and a labeled molecule to form a complex of the analyte, the unlabeled detection molecule, and the labeled molecule on the solid phase; and
   (e) a signal measurement process to detect the amount of the label in the complex in the presence of the solid phase in step (c) that immobilized the complex.
2. The method of claim 1(a), wherein said affinity binding solid phase comprises (i) a solid phase immobilized with an adaptor molecule, wherein the adaptor molecule immobilized having a capture molecule thereon for said specific analyte capture process, (ii) a solid phase immobilized with a capture molecule for said specific analyte capture process, or (iii) a solid phase immobilized with a complex of an adaptor molecule and a capture molecule for said specific analyte capture process.
3. The method of claim 1(a), wherein said affinity binding solid phase comprises polystyrene.
4. The method of claim 2, wherein said adaptor molecule comprises molecule capable of protecting the capture molecule from inactivation by a solid phase and capable of immobilizing the capture molecule on the solid phase.
5. The method of claim 2, wherein said adaptor molecule comprises Protein G.
6. The method of claim 2, wherein said capture molecule comprises antibody against said analyte.
7. The method of claim 1, wherein said analyte comprises low abundance protein.
8. The method of claim 1, wherein said fluid sample comprises cell lysate, blood, serum, plasma, salvia, urine, spinal fluid, other biological fluids, and fluids made from biological materials.
9. The method of claim 1(b), wherein said dissociation buffer comprises acidic or basic buffer capable of releasing said analyte immobilized into said liquid phase in step 1 (b), but not capable of blocking said analyte's physical adsorption on said non-affinity binding solid phase in step 1 (c).

10. The method of claim 1(d), wherein said labeled detection molecule comprises antibody against said analyte.

11. The method of claim 1(d), wherein said labeled molecule comprises labeled antibody against said unlabeled detection molecule.

12. A cell-based ELISA equivalent immunoassay for detecting and quantifying an analyte in a tissue or cells immobilized on a solid phase for eliminating non-specific background signals from the tissue or cells, the cell-based UTSIA, which comprises:
   (a) incubating the analyte in the tissue or cells immobilized on a solid phase with a labeled detection molecule or with an unlabeled detection molecule, to form an immobilized complex of the analyte and the labeled detection molecule or a complex of the analyte and the unlabeled detection molecule;
   (b) a dissociation process to release the labeled detection molecule or unlabeled detection molecule from the immobilized complex into a liquid phase via incubating the complex with a dissociation buffer;
   (c) a non-affinity physical absorption process to coat the labeled detection molecule or unlabeled detection molecule released in the liquid phase to a solid phase via incubating the labeled detection molecule or unlabeled detection molecule released in the liquid phase with another solid phase; and
   (d) a specific analyte determining process comprises (i) detecting the amount of the label in the labeled detection molecule immobilized in step (c), or (ii) incubating the unlabeled detection molecule immobilized in step (c) with a labeled molecule to form a complex of the unlabeled detection molecule and the labeled molecule on the solid phase, and then detecting the amount of the label of the labeled molecule.

13. The method of claim 12, wherein said analyte comprises protein.

14. The method of claim 12(a), wherein said solid phase comprises polystyrene.

15. The method of claim 12(a), wherein said unlabeled detection molecule comprises antibody against said analyte.

16. The method of claim 12(b), wherein said dissociation buffer comprises acidic or basic buffer capable of releasing the labeled detection molecule or unlabeled detection molecule immobilized into a liquid phase, but not capable of releasing the tissue or cells immobilized into the liquid phase.

17. The method of claim 12(c), wherein said solid phase comprises polystyrene.

18. The method of claim 12(d)(ii), wherein said labeled molecule comprises labeled antibody against said unlabeled detection molecule.

19. The method of claim 1(c), wherein said non-affinity binding solid phase comprises polystyrene.

20. The method of claim 12(a), wherein said labeled detection molecule comprises antibody against said analyte.

* * * * *